United States Patent [19]

Deguchi et al.

[11] Patent Number: 4,975,511

[45] Date of Patent: Dec. 4, 1990

[54] GLYCIDYL SULFONAMIDE COMPOUND

[75] Inventors: Yoshikuni Deguchi; Hiroshi Iwakiri; Kazunari Iwamoto; Kazuya Yonezawa, all of Kobe, Japan

[73] Assignee: Kanegafuchi Kagaku Kogyo Kabushiki Kaisha, Osaka, Japan

[21] Appl. No.: 432,643

[22] Filed: Nov. 7, 1989

Related U.S. Application Data

[62] Division of Ser. No. 291,027, Dec. 29, 1988, Pat. No. 4,908,459.

[30] Foreign Application Priority Data

Apr. 28, 1988 [JP] Japan .................................. 63-106607
Apr. 28, 1988 [JP] Japan .................................. 63-106608

[51] Int. Cl.$^5$ .................... C08G 59/30; C08G 77/14
[52] U.S. Cl. .......................................... 528/26; 528/27
[58] Field of Search ................................ 528/26, 27

[56] References Cited

U.S. PATENT DOCUMENTS

| | | | |
|---|---|---|---|
| 3,703,531 | 11/1972 | Cherubim et al. | 549/552 |
| 3,945,973 | 3/1976 | Smith et al. | 260/49 |
| 4,208,503 | 6/1980 | Martin | 528/27 X |
| 4,287,326 | 9/1981 | Mikami | 528/27 X |
| 4,436,787 | 3/1984 | Mikami et al. | 528/27 X |
| 4,619,949 | 10/1986 | Kistner | 528/27 X |
| 4,624,998 | 11/1986 | Keil | 528/27 X |
| 4,788,268 | 11/1988 | Lau et al. | 528/27 |
| 4,847,395 | 7/1989 | Deguchi et al. | 549/552 |

FOREIGN PATENT DOCUMENTS

| | | |
|---|---|---|
| 0000763 | 2/1979 | European Pat. Off. . |
| 0125826 | 11/1984 | European Pat. Off. . |
| 185921 | 9/1966 | U.S.S.R. . |

*Primary Examiner*—Earl Nielsen
*Attorney, Agent, or Firm*—Armstrong, Nikaido, Marmelstein, Kubovcik and Murray

[57] ABSTRACT

A novel glycidyl sulfonamide compound having a (poly)siloxane main chain of its molecule is used alone or in admixture with an epoxy resin to give a cured material being excellent in flexibility, elongation and impact strength without deteriorating thermal resistance, chemical resistance and water absorption thereof. An epoxy resin composition or a resin composition for an epoxy paint containing a glycidyl sulfonamide compound, the epoxy resin and a curling agent for epoxy resin provides a cured material or a coating film having the above-mentioned excellent properties. A process for preparing a glycidyl sulfonamide compound characterized in that subjecting an amine modified silicone having a (poly)siloxane main chain of its molecule to condensation reaction with a sulfonyl chloride to give a sulfonamide compound, which is subjected to an addition reaction with an epihalohydrin to give the glycidyl sulfonamide compound.

13 Claims, 6 Drawing Sheets

GLYCIDYL SULFONAMIDE COMPOUND

This is a division, of application Ser. No. 291,027 filed Dec. 29, 1988, now U.S. Pat. No. 4,980,459, issued Mar. 13, 1989.

BACKGROUND OF THE INVENTION

The present invention relates to (1) a novel glycidyl sulfonamide compound which is a liquid compound having a low viscosity and which provides a cured material having excellent flexibility and elongation, and more particularly to a glycidyl sulfonamide compound having siloxane or polysiloxane (hereinafter referred to as "(poly)siloxane") main chain in its molecule, and a process for preparing the same, (2) an epoxy resin composition comprising the glycidyl sulfonamide compound which provides a cured material having high thermal resistance and excellent toughness, and (3) a cured material prepared by curing the composition, and more particularly to an epoxy resin composition for epoxy paints which provides a coating film being excellent in flexibility and surface properties and a coating film formed by curing the composition.

Epoxy resins have been widely used for various purposes such as resins for paints, materials for electric apparatuses, adhesive agents, coating materials, materials used in civil engineering and construction industry and matrix materials for FRP because the epoxy resins have excellent properties such as thermal resistance, chemical resistance, adhesive properties and electrical insulating property. Especially, among the epoxy resins, an epoxy resin having at least one N,N-diglycidylamino group in its molecule (hereinafter referred to as "glycidylamine epoxy resin"), an epoxy resin which is prepared by means of a condensation reaction of a bisphenol with an epihalohydrin (hereinafter referred to as "epi-bis type epoxy resin"), and the like are used as adhesive agents having thermal resistance and matrix materials for prepreg used in spacecraft and aircraft since the cured materials prepared by curing with heat the epoxy resins together with curing agents exhibit both high thermal resistance and excellent adhesive property for a substrate.

However, generally, the cured epoxy resin does not have sufficient flexibility, toughness, impact strength, and the like, and does not sufficiently satisfy the mechanical properties required in various uses. Especially, a coating film of the epoxy resin does not sufficiently satisfy the mechanical properties required for paints.

In order to improve the mechanical properties of the epoxy resin such as flexibility and elongation, many attempts such as adding a flexibilizer to usual epoxy resin compositions in order to decrease the stress of the cured material prepared from the resin compositions and adding a filler to the compositions have been made.

Examples of the flexibilizer are, for instance, glycidyl compound prepared from oxyalkylene or polyoxyalkylene such as butanediol diglycidyl ether, glycerol triglycidyl ether, trimethylolpropane triglycidyl ether, polypropylene glycol diglycidyl ether (available from ASAHI DENKA KOGYO K.K. under the trade name of "ED-506", DAINIPPON INK AND CHEMICALS, INC. under the trade name of "Epiclon 707", and the like), polyethylene glycol diglycidyl ether (available from Nippon Oil and Fats Co., Ltd. under the trade name of "Epiol E-100"). These flexibilizers are used as reactive diluents. However, these flexibilizers have the defects that the amount of the flexibilizers should be adjusted to 5 to 20 parts by weight (hereinafter referred "parts by weight" to as "parts") because the properties of the epoxy resin by adding flexibilizers cannot be sufficiently exhibited when the amount is without the range of 5 to 20 parts. Accordingly, the thermal resistance of the cured material of the resin is considerably decreased.

Further, these glycidyl compounds prepared from alkylene ether or polyalkylene ether have the defects that when these compounds are co-cured with an epoxy resin, the obtained cured materials or coating films exhibit a deteriorated thermal resistance and chemical resistance, or an higher water absorption since these compounds have an ether linkage in the main chain of its molecule.

On the other hand, it is known that (poly)siloxane is remarkably excellent in thermal resistance, weatherability and oxidation deterioration resistance compared with (poly)ether because Si-O linkage has larger bonding energy than C-O linkage. The (poly)siloxane which is well-known as silicon oil is also excellent in water repellency, hydrophobic property and electric property, while the (poly)ether exhibits water absorption. The (poly)siloxanes are widely used as a heating medium, lubricating oil, and the like because the (poly)siloxanes have the above properties. For instance, a process in which a silicone rubber having a good stability against oxidation is blended or dispersed into an epoxy resin is proposed (Japanese Unexamined Patent Publication No. 21417/1983). However, it is known that (poly)siloxane has a defect that the (poly)siloxane is bled on the surface of the cured resin due to thermal history when the (poly)siloxane is merely blended and dispersed into an epoxy resin since (poly)siloxane is essentially poor in compatibility with as epoxy resin (Japanese Unexamined Patent Publication No. 116654/1987).

A process in which various rubber modifiers such as carboxyl group terminated butadiene-acrylonitrile rubber (CTBN) and amino group terminated butadiene-acrylonitrile rubber (ATBN) are added into an epoxy resin to form a cured material of which structure is like seam and islands in order to control the thermal resistance of the cured epoxy resin, is also proposed (refer to "Shinepokishi-jushi" (new epoxy resin) edited by Biroshi Kakiuchi and published by Shoko-do, and the like). These rubber modifiers, however, have a defect that long-term heat resistance of the cured material of the resin containing the modifiers is deteriorated because the rubber modifiers are very poor in oxidation resistance.

From the viewpoints mentioned above, a novel flexibilizer which imparts flexibility to cured materials or coating films of the epoxy resin without deteriorating the properties of the cured material or coating film of the resin, particularly, without increasing the water absorption, has been desired.

An object of the present invention is to provide a glycidyl compound which can be co-cured with an epoxy resin to give a cured material or a coating film having excellent toughness, flexibility and elongation, without largely deteriorating the thermal resistance of the cured epoxy resin.

These and other objects of the invention will be apparent to one skilled in the art upon consideration of the following description and appended claims.

SUMMARY OF THE INVENTION

It has now been found that a glycidyl sulfonamide compound having a (poly)siloxane main chain in its molecule can satisfy the above-mentioned purpose.

That is, in accordance with the present invention, there is provided a glycidyl sulfonamide compound (hereinafter referred to as "glycidyl sulfonamide compound (A)") which has a (poly)siloxane main chain in its molecule and which can be co-cured with an epoxy resin to give a cured material or a coating film of the epoxy resin having excellent toughness, flexibility, elongation and impact strength without largely deteriorating the properties such as thermal resistance, chemical resistance and water absorption, and a process for preparing the glycidyl sulfonamide compound (A). Further, in accordance with the present invention, there is provided an epoxy resin composition, that is, a resin composition for epoxy paint containing the glycidyl sulfonamide compound (A) and a cured material, particularly a coating film formed by curing the composition.

DETAILED DESCRIPTION

The present invention relates to (1) a novel glycidyl sulfonamide compound (A) represented by the general formula (I):

wherein each $R^1$ is a univalent hydrocarbon group having 1 to 20 carbon atoms, each $R^2$ is a bivalent hydrocarbon group having 1 to 6 carbon atoms, each $R^3$ is a univalent hydrocarbon groups having 1 to 6 carbon atoms, n is 0 or an integer of 1 to 70 and X is a hydrogen atom or a glycidyl group, (2) the process for preparing the glycidyl sulfonamide compound (A) represented by the general formula (I) comprising the steps of: subjecting a sulfonamide compound represented by the general formula (II):

wherein each $R^1$ is a univalent hydrocarbon group having 1 to 20 carbon atoms, each $R^2$ is a bivalent hydrocarbon group having 1 to 6 carbon atoms and each $R^3$ is a univalent hydrocarbon group having 1 to 6 carbon atoms, n is 0 or an integer of 1 to 70, to an addition reaction with an epihalohydrin and reacting the reaction mixture with a caustic alkali,

(3) an epoxy resin composition, particularly, an epoxy resin coating composition comprising (A) the above-mentioned glycidyl sulfonamide compound represented by the general formula (I), (B) an epoxy resin and (C) an agent for curing epoxy resins, and (4) a cured product thereof.

The above-mentioned glycidyl sulfonamide compound (A) is contained in the composition in order to improve flexibility and surface property of the cured product, particularly, the cured film.

The glycidyl sulfonamide compound (A) of the present invention can be prepared, for instance, according to a method described in Japanese patent application No. 161505/1987, and the like.

In the first step of the process for preparing the glycidyl sulfonamide compound (A), the sulfonamide compound (II) is prepared. That is, as a starting compound, an amine-modified silicone represented by the general formula (III):

wherein each $R^2$ is a bivalent hydrocarbon group having 1 to 6 carbon atoms, each $R^3$ is a univalent hydrocarbon group having 1 to 6 carbon atoms, and n is 0 or an integer of 1 to 70, is subjected to condensation reaction with a sulfonyl chloride represented by the general formula (IV):

$R^1SO_2Cl$ (IV)

wherein $R^1$ is a univalent hydrocarbon group having 1 to 20 carbon atoms in the presence of a dehydrochlorination agent or a condensing agent such as sodium hydroxide to give the sulfonamide compound represented by the above-mentioned general formula (II), having a (poly)siloxane main chain of the molecule.

The amine modified silicone represented by the general formula (III) forms a main chain of the glycidyl sulfonamide compound (A) of the present invention. It is necessary that the amine-modified silicone (III) has at least one, preferably 5 to 70 siloxane bond, and has aminoalkyl groups having 1 to 6 carbon atoms at both ends of the molecule. The substituent on the silicon atom is not limited so long as it is a hydrocarbon group having 1 to 6 carbon atoms. An amine-modified silicone wherein the above-mentioned substituent is methyl group, ethyl group, phenyl group, or the like is most general and easily available. Examples of the amine modified silicone are, for instance, 1,3-bis(4-aminobutyl)-tetramethyldisiloxane, 1,3-bis(4-aminopropyl)-tetramethyldisiloxane, and the like, in addition, a silicone oligomer in which both ends of the molecule are modified with amines (hereinafter referred to as "amine terminated silicone oligomar") available from CHISSO CORPORATION under the trade name of "SILAPLANE", and these are suitably employed. The amine modified silicones represented by the general formula (III) can be used alone or in admixture thereof.

Examples of the sulfonyl chloride represented by the general formula (IV) are, for instance, aliphaticsulfonyl chloride such as methanesulfonyl chloride (corresponding to the compound, wherein $R^1$ represents methyl group), ethanesulfonyl chloride ($R^1$: ethyl group); aromaticsulfonyl chloride such as benzenesulfonyl chloride ($R^1$: phenyl group), o- or p- toluenesulfonyl chloride ($R^1$: tolyl group), 2,4-or 2,5-dimethylbenzenesulfonyl chloride ($R^1$: dimethylphenyl group) and 1-or 2-naphthalenesulfonyl chloride ($R^1$: naphthyl group); and the like. Among them, the aromatic sulfonyl chlorides are easily available as industrial sources. The sulfonyl chloride represented by the general formula (IV) can be used alone or in admixture thereof.

The used amount of the sulfonyl chloride represented by the general formula (IV) is from 0.9 to 1.1 equivalents, preferably from 0.95 to 1.05 equivalents, more preferably 1.0 equivalent per amine equivalent of the amine modified silicone represented by the general formula (III). When the amount of the sulfonyl chloride (III) is outside of the above-mentioned range, the epoxy equivalent of the glycidyl sulfonamide compound (A) obtained by the following reaction is increased, which is not preferable.

As the condensing agent, a caustic alkali is preferably used, since it is available at a low price. It is preferable that the condensing agent is used in an amount of the same equivalent as the sulfonyl chloride from the viewpoints of the purity and yield of the product.

The condensation reaction can be carried out in the absence of solvent, however, it is preferable that an inactive solvent such as an aromatic hydrocarbon or a halogenated hydrocarbon is used as the solvent for controlling the viscosity of the reaction mixture and temperature of the reaction system.

The condensation reaction of the first step of the process is usually carried out at a temperature of 0° to 70° C. for 1 to 2 hours, then an ionic impurity is removed from the reaction mixture, and the reaction solvent is distilled away in case of using it. The obtained product can be used in the second step of the process as it is.

The second step of the process is that the sulfonamide compound (III) having (poly) siloxane in the main chain of the molecule obtained in the first step is subjected to addition reaction with an epihalohydrin.

Examples of the epihalohydrin are, for instance, epichlorohydrin, β-methylepichlorohydrin, epibromohydrin, epiiodohydrin, and the like. Epichlorohydrin is preferable since it can be industrially easily obtained. The amount of the epihalohydrin is one or more equivalents per sulfonamide group of the sulfonamide compound. It is preferable that the amount is from 2 to 10 equivalents per sulfonamide group of the sulfonamide to inhibit the side reaction.

The addition reaction proceeds very slowly or hardly proceeds in the absence of the catalyst. Accordingly, it is very preferable that at least one phase-transfer catalyst selected from the group consisting of quaternary ammonium salt, quaternary phosphonium salt and quaternary arsonium salt is used. Examples of such phase-transfer catalysts are, for instance, tetramethylammonium chloride, tetraethylammonium bromide, triethylmethylammonium chloride, triphenylmethylphosphonium chloride, tetraphenylphosphonium chloride and the like. The amount of the phase-transfer catalyst can be selected in the range of 0.01 to 100% by mole, preferably 1 to 10% by mole, based on the sulfonamide compound. The reaction temperature and the period of time for the addition reaction depend upon the amount of the catalyst used. Usually, the reaction is carried out at 70° to 120° C. for 0.5 to 12 hours, preferably at 100° to 120° C. for 3 to 8 hours.

The third step of the process is that the caustic alkali is added to the product obtained by the addition reaction of the second step, and the mixture is subjected to dehydrohalogenation reaction. The phasetransfer catalyst used in the addition reaction can be used as the catalyst for the dehydrohalogenation reaction. As the caustic alkali, sodium hydroxide, potassium hydroxide, calcium hydroxide, magnesium hydroxide, barium hydroxide, or the like can be used. Among them, sodium hydroxide is preferable since it is easily available as an industrial source. The caustic hydroxide can be used in the form of a solid or an aqueous solution. The aqueous solution of the caustic hydroxide is preferable because it can be easily handled. The amount of the caustic alkali is from 1.0 to 2.0 equivalents, preferably from 1.1 to 1.5 equivalents based on the sulfonamide group. The dehydrohalogenation reaction is carried out at 20° to 70° C. for 10 minutes to 3 hours, preferably at 40° to 60° C. for 0.5 to 2.0 hours.

The dehydrohalogenation reaction is usually carried out in the epihalohydrin. The excess amount of the epihalohydrin can be optionally distilled away and recovered prior to the reaction. In this case, it is preferable that inactive solvent, for instance, ketones such as methyl ethyl ketone, methyl isobutyl ketone and cyclohexanone; aromatic hydrocarbons such as benzene, toluene and xylene; or halogenated hydrocarbons such as chloroform and methylene chloride is used as a diluent of the glycidyl sulfonamide compound.

After the reaction is completed, the produced salt is removed from the reaction mixture by filtering centrifuging or washing with water, and then the unreacted epihalohydrin or the inactive solvent is distilled away to give a glycidyl sulfonamide compound (A) of the present invention.

The glycidyl sulfonamide compound (A) has the general formula (I):

In the general formula (I), $R^1$ is a univalent hydrocarbon group having 1 to 20 carbon atoms. Examples of the hydrocarbon group $R^1$ are, for instance, aliphatic hydrocarbon groups such as methyl group, ethyl group, n-propyl group and isopropyl group; aromatic hydrocarbon groups such as phenyl group, tolyl group, dimethylphenyl group, naphthyl group, o-, m- or p- cumenyl group and mesityl group; and the like. Among them, the compounds having methyl group, ethyl group, phenyl group, tolyl group, dimethylphenyl group, naphthyl group or the like as $R^1$ in the formula (I) are preferable because the raw material of the compounds are easily available. The compound having the aromatic hydrocarbon group such as phenyl group, tolyl group, dimethylphenyl group or naphthyl group as $R^1$ is more preferable since the raw material of the compound is easily available as industrial source. When the compound has the univalent hydrocarbon group having more than 20 carbon atoms as $R^1$, the raw material of the compound is not easily available.

In the general formula (I), $R^2$ is a bivalent hydrocarbon group having 1 to 6 carbon atoms. Examples of the hydrocarbon group $R^2$ are, for instance, mathylene group, ethylene group, trimethylene group, tatramethylene group, and the like. Among them, the compound having trimethylene group as $R^2$ is preferable because the raw material of the compound is easily available.

In the general formula (I), $R^3$ is a univalent hydrocarbon group having 1 to 6 carbon atoms. Examples of the hydrocarbon group $R^3$ are, for instance, methyl group, ethyl group, phenyl group, and the like. The compound having the group as $R^3$ is more preferable because the raw material of the compound is easily available.

In the general formula (I), n is 0 or an integer of 1 to 70. The compound represented by the general formula (I) wherein n is an integer of 4 to 65 is more preferable because the compound and the spoxy resin can form a suitable phase separation structure. When n is an integer of more than 70, the compound is completely separated from the epoxy resin, so it is very difficult to be dispersed uniformly it into the epoxy resin.

In the general formula (I), X is hydrogen atom or glycidyl group. Generally, the glycidyl sulfonamide compound (A) represented by the general formula (I) is a mixture of the compound (A) having the formula (I) wherein X is hydrogen and the compound (A) having the formula (I) wherein X is glycidyl group. A conversion of N—H in the sulfonamide into glycidyl group is defined as "degree of epoxidation". The degree of epoxidation is preferably not less than 70%, more preferably not less than 80%. The compound having a low degree of epoxidation is poor in storage stability and is easily increased in viscosity.

In the general formula (I), the number of each $R^1$ and $R^2$ is 2. The groups $R^1$ are the same or different and the group $R^2$ are the same or different. In the general formula (I), the number of $R^3$ is 2n+4, and the groups $R^3$ are the same or different. The compound having the formula (I) in which two $R^3$ groups are the same and (2n+4) $R^3$ groups are the same is easily available.

Examples of the glycidyl sulfonamide compound (A) represented by the general formula (I) are, for instance, a compound represented by the general formula:

wherein $R^2$, $R^3$, n and X are as defined above, a compound represented by the general formula:

wherein $R^2$, $R^3$, n and X are as defined above, a compound represented by the general formula:

wherein $R^1$, $R^3$, n and X are as defined above, and the like. As further concrete examples of the compound (A), compounds represented by the following general formulae (i) to (iv) are exemplified.

wherein n is an integer of 5 to 20.

wherein n is an integer of 5 to 20.

Among them, the glycidyl sulfonamide compound represented by the general formula (ii) and the glycidyl sulfonamide compound represented by the general formula (iv) are preferable because the raw materials of these compounds can be easily obtained.

The thus obtained glycidyl sulfonamide compound (A) is colorless or light yellow liquid and has a low viscosity (about 1 to 50P) at room temperature. With respect to the glycidyl sulfonamide compound (A), it can be confirmed that the glycidyl group is introduced into its molecule by the experimental results of an absorption band of 905 to 930 cm$^{-1}$ of infrared absorption spectrum, a characteristic absorption of 2.5 to 4.0 ppm of proton nuclear magnetic resonance spectrum and determination of epoxy equivalent weight by hydrochloric acid-pyridine method.

The glycidyl sulfonamide compound (A) obtained in the above-mentioned process can be cured together with the curing agent (C), alike usual epoxy resins. The obtained cured product is elastic. The curing agent (C) is not limited so long as a curing agent is usually used when curing epoxy resins. Examples of the curing agent (C) are, for instance, acid anhydrides such as tetrahydrophthalic anhydride, methyltetrahydrophtnalic anhydride, hexahydrophthalic anhydride, methylhexahydrophthalic anhydride, nadic methyl anhydride, pyromellitic anhydride, trimellitic anhydride and benzophenonetetracarboxylic acid anhydride; acylic aliphatic polyamines such as diethylenetriamine and triethylenetetramine; alicyclic amines such as menthenediamine and isophoronediamine; aromatic polyamines such as (m- or p-) xylylenediamine, (m- or p-) phenylenediamine, 4,4'-diaminodiphenylmethane and 4,4'-diaminodiphenyl sulfone; tertiary amines such as benzyldimethylamine and 2,4,6-tris(dimethylaminomethyl)-phenol; polyamides; imidazoles such as 2-methylimidazole and 2-ethyl-4-methylimidazole; Lewis acid-amine complex typified by boron trifluorideamine complex; dicyandiamide and its derivatives; polyphenols such as cresol novolak, phonol novolak, polyvinylphenol and primary condensation product of phenol-formaldehyde; polymercaptans; and the like. Among these curing agents (C), the agent which is in liquid state at room temperature is more preferable because it is easy to handle.

The glycidyl sulfonamide compound (A) of the present invention can be optionally mixed and co-cured together with the other epoxy compound. The kind of the epoxy compound to be mixed with the compound (A) is not limited, and mixing ratio of the glycidyl sulfonamide compound (A) and the epoxy compound can be suitably adjusted.

The epoxy resin composition or the epoxy resin coating composition of the present invention comprises the glycidyl sulfonamide compound (A) represented by the general formula (I), an epoxy resin (B) and a curing agent (C).

The epoxy resin composition or the epoxy resin coating composition of the present invention can contain two or more kinds of the glycidyl sulfonamide compounds (A).

The above-mentioned epoxy resin (B) is an epoxy resin having not less than 2 epoxy groups in its molecule, and preferably having the epoxy equivalent weight of 100 to 700 g/equivalent.

Examples of the epoxy resin (B) are, for instance, glycidyl amine epoxy resins prepared from amines such as 4,4'- or 3,4'-diaminodiphenylmethane, mor p-aminophenol, aminonaphthol and m-xylylenediamine (for instance, available from TOHTO KASEI CO., LTD. under the trade name of "YH-434", or from Sumitomo Chemical Company, Limited under the trade name of "ELM-120"); epibis type epoxy resins (for instance, available from Yuka Shell Epoxy Co., Ltd. under the trade name of "Epikote 807, 828 or 1001"); epi-bis type epoxy resins having brominated aromatic nucleus (for instance, available from TOHTO KASEI CO., LTD. under the trade name of "YDB-400"); novolak epoxy resins such as glycidyl derivatives of phenol novolak and glycidyl derivative of cresol novolak (for instance, available from NIPPON KAYAKU CO., LTD under the trade name of "EOCN-102"); polyglycidyl ether epoxy resins typified by novolak epoxy resin having brominated aromatic nucleus; polyglycidyl estere of acids such as phthalic acid, cyclohexanedicarboxylic acid and the like; heterocyclic epoxy resins such as hydantoin epoxy resin and triglycidyl isocyanurate; and alicyclic epoxy resins. The above-mentioned epoxy resins can be used alone or in admixture thereof. Among these epoxy resins, the epi-bis type epoxy resins are preferable from the viewpoint that the resins have well-balanced properties, and the glycidyl amine epoxy resins are preferable from the viewpoint that the resins have excellent thermal resistance. Especially, it is preferable that the epoxy resin (B) is an epoxy resin having at least one N,N-diglycidylamino group in one molecule, such as tetraglycidyldiaminodiphenylmethane and/or a condensation product thereof because the defect that the cured coating film prepared by the epoxy resin is too hard and brittle, can be remarkably improved by adding the glycidyl sulfonamide compound (A) represented by the general formula (I) into the resin.

In case of using the glycidyl sulfonamide compound (A) with the epoxy resin (B), the weight ratio of the compound (A) to the epoxy resin (B) is not limited. It is preferable that the weight ratio of the compound (A) to the resin (B) from 0.01:99.99 to 50:50, more preferably from 0.1:99.9 to 20:80. The weight ratio can be selected depending on its use.

In case of using the above-mentioned glycidyl sulfonamide compound (A) together with the epoxy resin (B), a curing agent for curing epoxy resins (C) can be used without any limitation. There are exemplified, as the curing agent (C), the same curing agents used in the case that the glycidyl sulfonamide compound (A) of the present invention is cured without being mixed with the epoxy resin (B). That is, examples of the curing agent (C) are, for instance, acid anhydrides such as tetrahydrophthalic anhydride, methyltetrahydrophthalic anhydride, hexahydrophthalic anhydride, methylhexahydrophthalic anhydride, nadic methyl anhydride, pyromellitic anhydride, trimellitic anhydride and benzophenonetetracarboxylic acid anhydride; chain aliphatic polyamines such as diethylenetriamine and triethylenetetramine; alicyclic amines such as menthenediamine and isophoronediamine; aromatic polyamines such as (m- or p-) xylylenediamine, (m- or p-) phenylenediamine, 4,4'-diaminodiphenylmethane, and 4,4'-diaminodiphenyl sulfone; tertiary amines such as benzyldimethylamine and 2,4,6-tris(dimethylaminomethyl)phenol; polyamides; imidazoles such as 2-methylimidazole and 2-ethyl-4-methylimidazole; Lewis acid-amine complex typified by boron trifluoride-amine complex; dicyandiamide and its derivatives; polyphenols such as cresol novolak, phenol novolak, polyvinylphenol and primary condensation product of phenol-formaldehyde; polymercaptans; and the like.

Among these curing agents, the aromatic polyamide having at least 2 primary amine groups in the molecule, such as 4,4'- or 3,4'-diaminodiphenylsulfone or 4,4'- or 3,4'-diaminodiphenylmethane is preferable since the cured product is excellent in thermal resistance; the aliphatic amine curing agent is preferable since the composition can be cured quickly even at a low temperature; and the acid anhydride is preferable since the cured product is excellent in thermal resistance and electric property.

In case of using the epoxy resin composition of the present invention as a paint which can be cured without heating, it is preferable that the aliphatic amine curing agent is used as the curing agent since the composition can be cured at a low temperature, accordingly, at a room temperature. In case of using the epoxy resin composition as a paint which can be cured with heating, it is preferable that the aromatic amine curing agent or acid anhydride curing agent is used as the curing agent since the cured film having excellent film properties (such as thermal resistance and durability) can be obtained.

The amount of the curing agent (C) depends on the kind of the curing agent (C), it is preferable that the curing agent (C) is used in an amount known as the most suitable amount of the curing agnet. For instance, in case of using the aliphatic (poly)amine curing agent, the alicyclic (poly)amine curing agent, aromatic (poly)amine curing agent or the polyphenol, the agent is preferably used in an amount of 0.8 to 1.2 equivalents, more preferably 0.9 to 1.1 equivalents based on one equivalent of the total of epoxy groups of the glycidyl sulfonamide compound (A) and the epoxy group of the epoxy resin (B). In case of using acid anhydride curing agent, the agent is preferably used in an amount of 0.7 to 1.0 equivalent, more preferably 0.8 to 0.9 equivalent based on one equivalent of the total of epoxy groups of the glycidyl sulfonamide compound (A) and the epoxy group of the epoxy resin (B). A coating film having an excellent property can be obtained by using the curing agent in such an amount. Further, in case of using the tertiary amine, the imidazole, the Lewis acid-amine complex or the dicyandiamide as the curing agent, the agent can be used in an amount of 1 to 10 parts based on 100 parts of the glycidyl sulfonamide compound (A) and the epoxy resin (B). A cured product having an excellent property can be obtained by using the curing agent in such an amount.

The epoxy resin composition or the epoxy resin coating composition of the present invention may contain, as occasion demands, various additives such as an accelerator used for improving the curing rate of the composition; a thermoplastic resin used for improving the property of cured product or film in an amount within a range which does not deteriorate the properties of the composition; a monomer used in thermosetting resin or a thermosetting resin other than the epoxy resin used for controlling the curing rate and for improving the property of the film; a filler used for decreasing curing shrinkage; a coupling agent used for improving adhesive property against a substrate; an organic or inorganic pigment for coloring; an organic solvent used for adjusting the viscosity of the composition; a reinforcement; a leveling agent; a fire retardant; and a stabilizer.

Examples of the above-mentioned accelerator are, for instance, tertiary amines such as benzyldimethylamine and 2,4,6-tris(dimethylaminomethyl)phenol; imidazole; and the like.

Examples of the above-mentioned thermoplastic resin which is generally employed are, for instance, xylene resin, ketone resin, dicyclopentadiene resin, and the like.

As for the above-mentioned monomer used in the thermosetting resin or the thermosetting resin other than the epoxy resin, a monomer or a resin which can be cured together with the composition of the present invention is preferable. Examples of the monomer or the resin are, for instance, unsaturated polyester resins, vinyl monomers, and the like.

Examples of the above-mentioned filler are, for instance, silica, talc, and the like.

Examples of the above-mentioned reinforcement are, for instance, glass fiber, carbon fiber, aramid fiber, and the like.

The epoxy resin composition of the present invention is usually prepared by mixing at once the glycidyl sulfonamide compound (A), the epoxy resin (B), the curing agent (C) and, if necessary, the other components.

When it is difficult to mix these components uniformly, the composition can be prepared by previously dissolving the components into an inactive solvent to mix, then removing the solvent.

In order to improve the uniformity of the cured product, previously an adduct is prepared by reacting the glycidyl sulfonamide compound (A) with the curing agent (C) and then to the adduct is added the epoxy resin (B) to give the composition of the present invention.

The thus prepared composition can be cured at a room temperature, and in order to obtain a cured product having excellent thermal resistance, it is preferable that the composition is finally heated at a temperature of 100° to 200° C. for 1 to 5 hours. The thus obtained cured product can be further improved in the thermal resistance by further post-curing the product at a temperature of 150° to 250° C.

The cured product usually is cloudy and has a structure having micro dispersed (poly)siloxane in the resin.

Since the epoxy resin composition of the present invention contains, as the component, the glycidyl sulfonamide compound (A) having a (poly)soloxane main chain and after curing the composition, it forms a micro phase separation as a rubber component, the cured product of the epoxy resin composition is remarkably improved in toughness in comparison with cured products of conventional epoxy resin composition.

When usual flexibilizers are employed, it is necessary that the flexibilizers are used in an amount of 10 to 20 parts based on 100 parts of the total amount of the epoxy resin and the flexibilizer. When using the flexibilizer, the thermal resistance of the cured product deteriorates in exchange for flexibility. In the epoxy resin composition of the present invention, however, even though the glycidyl sulfonamide compound (A) is used in the same as or more than the amount of conventional flexibilizers, the thermal resistance of the cured material is little lowered. Further, even though the glycidyl sulfonamide compound (A) is used in a small amount such as 5 parts or less based on 100 parts of the total amount of the epoxy resin (B) and the compound (A), the mechanical properties of the cured material such as flexural strength and Izod impact strength can be remarkably improved without substantial deterioration of the thermal resistance thereof.

Since the glycidyl sulfonamide compound (A) of the present invention has the above-mentioned excellent properties which cannot be obtained in usual epoxy resins or flexibilizers, the compound (A) is useful as, for instance, casting materials for electric or electronic apparatuses, adhesive agents, matrix materials for laminated materials or FRP. Especially, since the glycidyl sulfonamide compound (A) has both excellent thermal resistance and toughness and is effective in decreasing internal stress of the cured product, it is expected to be used in a field of materials to which mechanical or thermal stresses are repeatedly given.

The epoxy resin coating composition of the present invention is usually prepared by mixing the glycidyl sulfonamide compound (A), the epoxy resin (B), the curing agent (C) and, if necessary, the other components in a suitable vessel with a stirrer such as brabender, kneader or mixer, and are mixed together. In such a case, the adding or mixing order of the components is not limited, and the components can be mixed at once. During the mixing procedure, the temperature of the composition is suitably adjusted, and usually the mixing is carried out at a temperature of 0° to 50° C. The thus prepared composition is applied by a spray, coater or brush, and is cured to give a film. The curing reaction can proceed at a room temperature, however, in order to obtain a cured film having excellent thermal resistance, it is preferable that it is cured, for instance, at a temperature of 80° to 200° C.

When the glycidyl sulfonamide compound (A) is used together with the epoxy resin (B), since the glycidyl sulfonamide compound (A) has a glycidyl group in the molecule, the mixture of the compounds (A) and (B) can be cured by using the same curing agent as the curing agent for an epoxy resin, and the curing agent can be incorporated into the curing system.

With proceeding the curing reaction of the glycidyl sulfonamide compound (A) and the epoxy resin (B), in some cases, they form a structure having phase separation in micron order, however, they do not bleed, since they are chemically combined with each other.

The film prepared from the epoxy resin coating composition of the present invention is excellent in the properties such as toughness, flexibility, water repellency and lubrication.

The present invention is more specifically described and explained by means of the following Examples in which all parts are by weight unless otherwise noted. It is to be understood that the present invention is not limited to the Examples, and various changes and modification may be made in the invention without departing from the spirit and scope thereof.

PREPARATION EXAMPLE 1

[Preparation of sulfonamide compound (A-1)]

Figure 1:
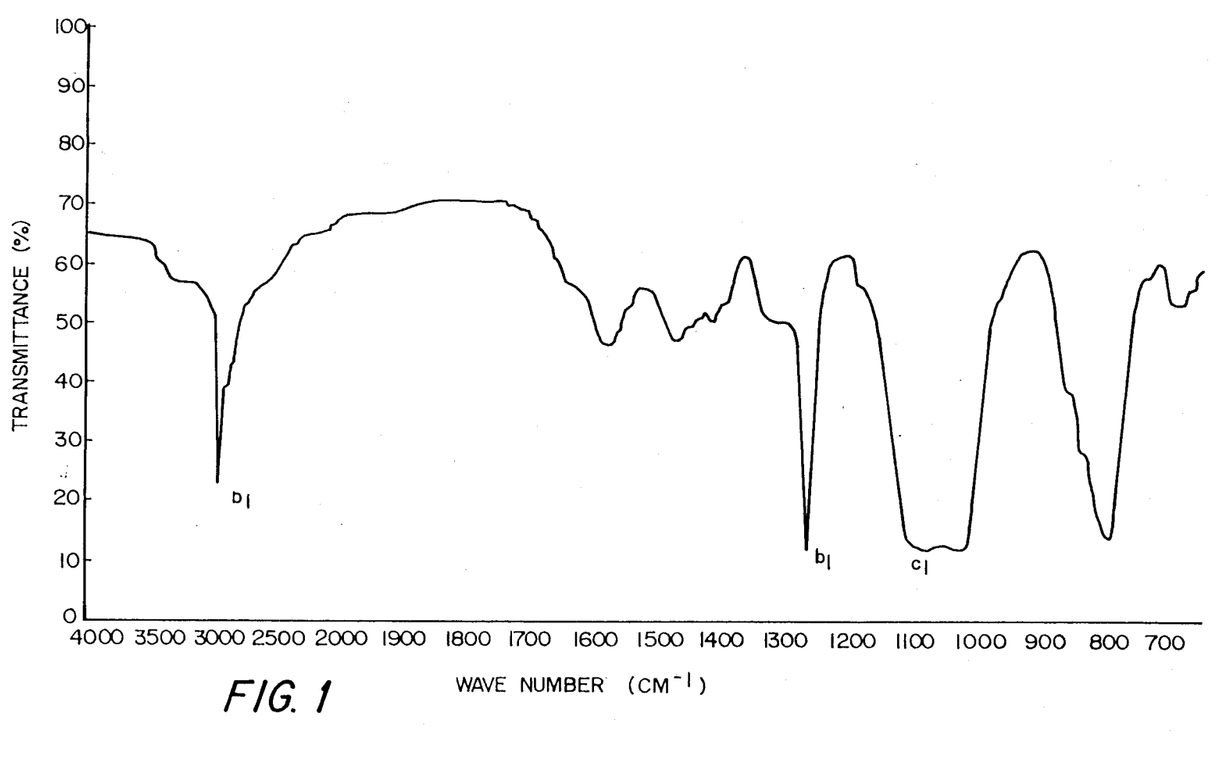
FIG. 1, 2 and 3 are diagrams showing the results of infrared absorption spectrum of amine terminated silicone used as a raw compound in Preparation Example 1, sulfonamide compound (A-1) prepared in Preparation Example 1 and glycidyl sulfonamide compound (A-1), respectively.
Figure 2:
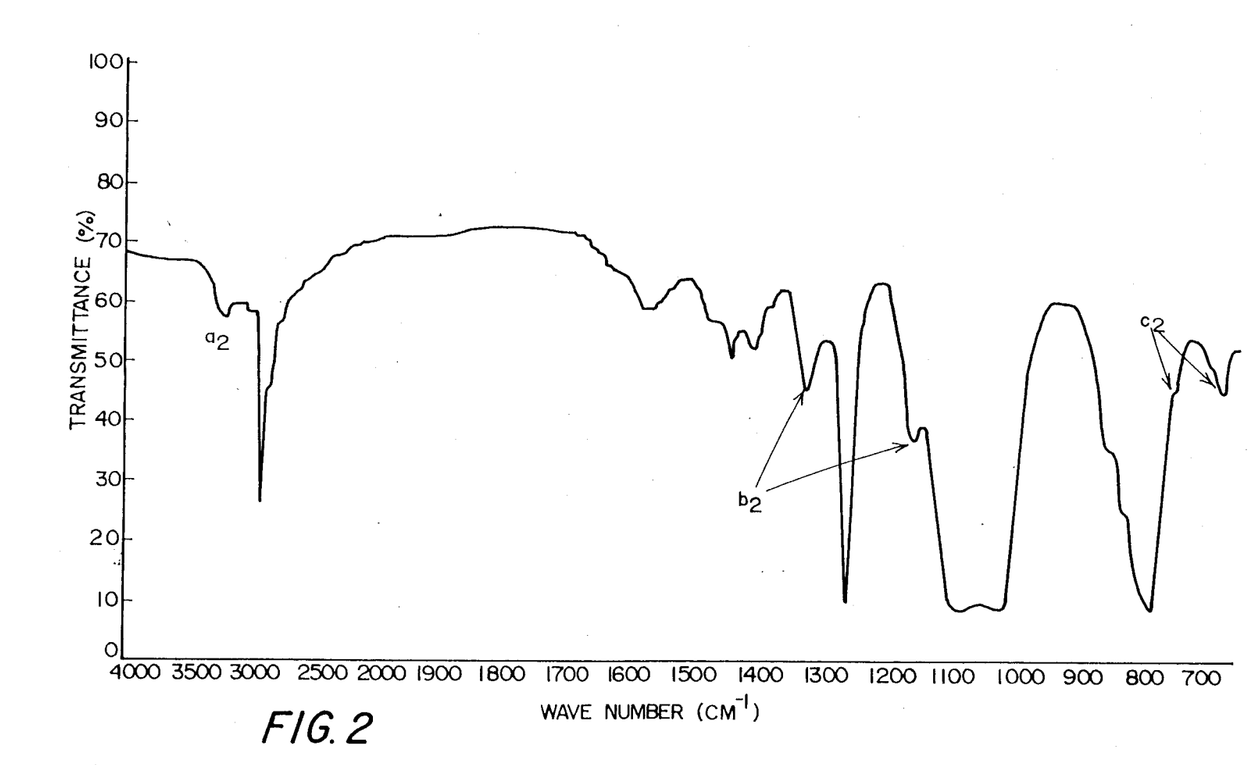
Figure 4:
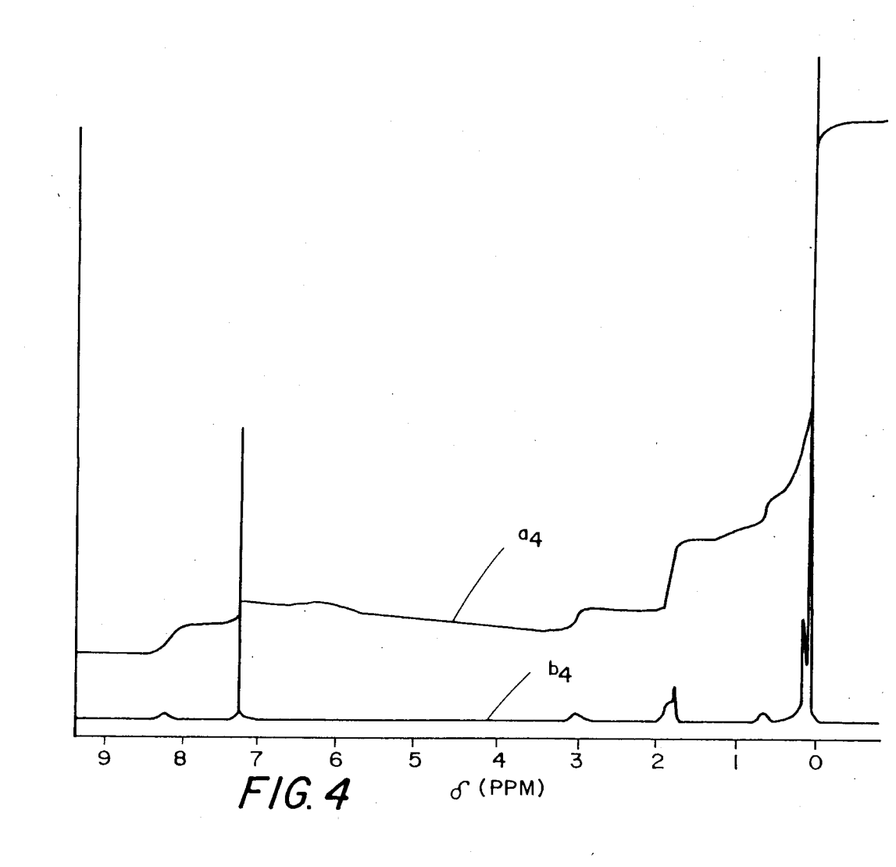
FIG. 4, 5 and 6 are diagrams showing the results of proton nuclear magnetic resonance spectrum of amine terminated silicone used as a raw compound in Preparation Example 1, sulfonamide compound (A-1) and glycidyl sulfonamide compound (A-1), respectively.
Figure 5:
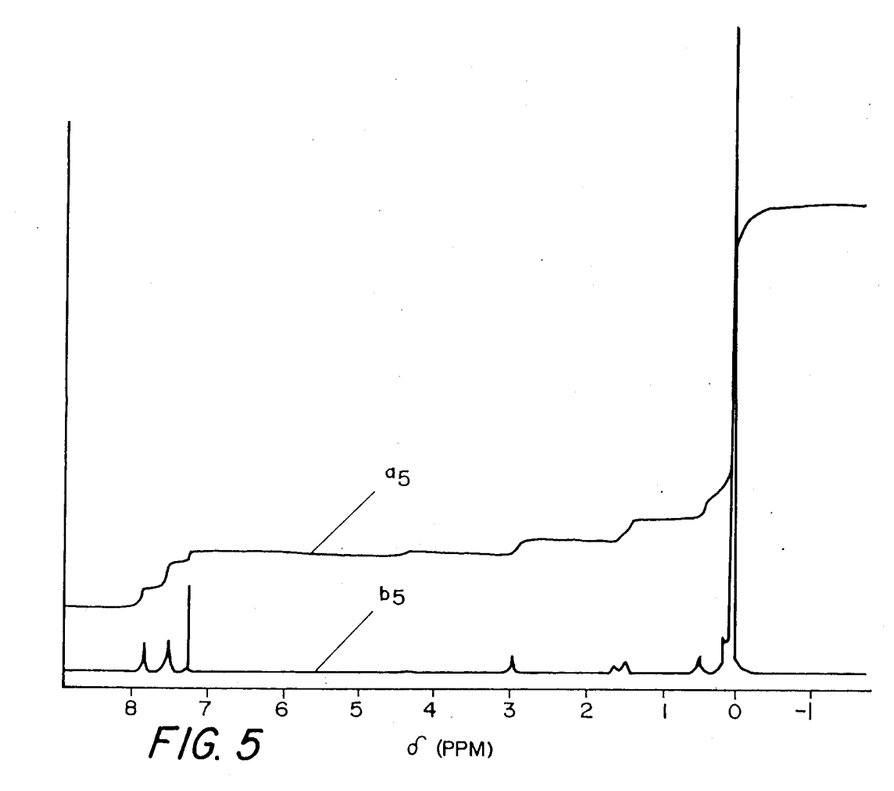

A four necked flask having a volume of 200 ml was charged with 49.30 g (amino group:100 millimoles) of an amine terminated silicone oligomer (available from CHISSO CORPORATION under the trade name of "SILAPLANE FM-3311", amine equivalent: 493 g/equivalent, corresponding to the compound represented by the general formula (III) wherein $R^2$, $R^3$ and n represent trimethylene group, methyl group and an integer of 9 to 10, respectively. The identifying data are shown in FIG. 1 and FIG. 4. FIG. 1 is a diagram showing the results of infrared adsorption spectrum of the amine terminated silicone (measurement range:650 to 4000 $cm^{-1}$, measured neat). FIG. 4 is a diagram showing the results of proton nuclear magnetic resonance spectrum of the amine terminated silicon (NMR: 300 MHz, solvent: $CDCl_3$). In FIG. 1, the sharp absorption $a_1$ of IR at 2950 $cm^{-2}$ indicates —(CH$_2$)$_3$ group, the strong absorption $b_1$ at 1260 and 790 $cm^{-1}$ indicates Si—$CH_3$ group, the strong broad absorption $C_1$ at 1020 to 1090 $cm^{-1}$ indicates group, and the weak broad absorption at 3400 $cm^{-1}$ indicates —$NH_2$. In FIG. 4, the large peak signals near 0.10 to 0.20 indicate protons of and the sharp signal at 1.80 ppm indicates amino end group ($a_4$ and $b_4$ indicate integral intensity and δ, respectively.), 20 ml of chloroform and 20 ml (100 millimoles) of 5N aqueous solution of sodium hydroxide. Into the mixture, 17.66 g (100 millimoles) of benzenesulfonyl chloride was added dropwise over 10 minutes with externally cooling with ice water. Then, the mixture was heated to 60° C., and was stirred for 2 hours. Water layer of the mixture was removed by decantation, and the chloroform was distilled away to give 63.15 g of a sulfonamide compound having a siloxane main chain of (hereinafter referred to as "sulfonamide compound (A-1)"). It was found from a material balance of the procedure that the reaction almost quantitatively proceeded. The sulfonamide compound (A-1) was a liquid compound having a low viscosity at a room temperature. The identifying data of the obtained sulfonamide compound (A-1) are shown in FIG. 2 and FIG. 5. FIG. 2 is a diagram showing the results of infrared adsorption spectrum of the sulfonamide compound (A-1) (measurement range: 650 to 4000 $cm^{-1}$, measured: neat). FIG. 5 is a diagram showing the results of proton nuclear magnetic resonance spectrum of the sulfonamide compound (A-1) (NMR: 300 MHz, solvent: $CDCl_3$). In FIG. 2, the newly appeared peaks of absorption of IR are $a_2$ at 3250 $cm_{-1}$:

$b_2$ at 1155 and 1325 cm$^{-1}$: —SO$_2$—N<, $c_2$ at 690 and 750 cm$^{-1}$:

respectively. In FIG. 5, the signals of near 7.55 and 7.88 ppm are corresponding protons in benzene ring and indicate monosubstituted benzene and the signal of 4.45 ppm indicates proton in sulfonamide ($a_5$ and $b_5$ indicate integral intensity and $\delta$, respectively).

PREPARATION EXAMPLE 2

[Preparation of sulfonamide compound (A-2)]

The same procedure as in Preparation Example 1 was repeated except that 247.9 g of an amine terminated silicone oligomer EM-3321 (available from CHISSO CORPORATION under the trade name "SILA-PLANE FM-3321", amine equivalent: 2479 g/equivalent, corresponding to the compound represented by the general formula (III), wherein $R^2$, $R^3$ and n represent trimethylene group, methyl group and an integer of 63 to 64, respectively, instead of the amine terminated silicone oligomer FM-3311 to give 258.5 g of a sulfonamide compound having a siloxane main chain of the molecule (hereinafter referred to as "sulfonamide compound (A-2)").

The sulfonamide compound (A-2) was also a liquid compound having a low viscosity.

EXAMPLE 1

[Preparation of glycidyl sulfonamide compound (A-1)]

To 63.15 g of the sulfonamide compound (A-1) prepared in Preparation Example 1, were added 46.3 g of epichlorohydrin and 1.14 g of benzyltriethyl ammonium chloride (catalyst for reaction), then the mixture was reacted at 100° to 110° C. for 4 hours. The reaction mixture was cooled to 50° C., and 120.0 ml of 5N aqueous solution of sodium hydroxide was added to the reaction mixture dropwise over 10 minutes with stirring violently. After the addition, the mixture was further stirred for 2 hours. The water layer of the mixture containing salts was removed by decantation, and the organic layer was washed 4 times with 100 ml of deionized water. The excess epichlorohydrin was distilled away under reduced pressure to give 68.23 g of a glycidyl sulfonamide compound (hereinafter referred to as "glycidyl sulfonamide compound (A-1)") (corresponding to the compound represented by the general formula (I) wherein $R^1$, $R^2$, $R^3$ and n represent a phenyl group, a trimethylene group, a methyl group and an integer of 11 to 12, respectively). With respect to the glycidyl sulfonamide compound (A-1), the viscosity was 2.8 poise at 25° C., the epoxy equivalent weight determined by means of hydrochloric acid-pyridine method was 729. The degree of epoxidation calculated from the epoxy equivalent weight was 94.5% and the yield based on the theoretical yield was 99.0%.

Figure 3:
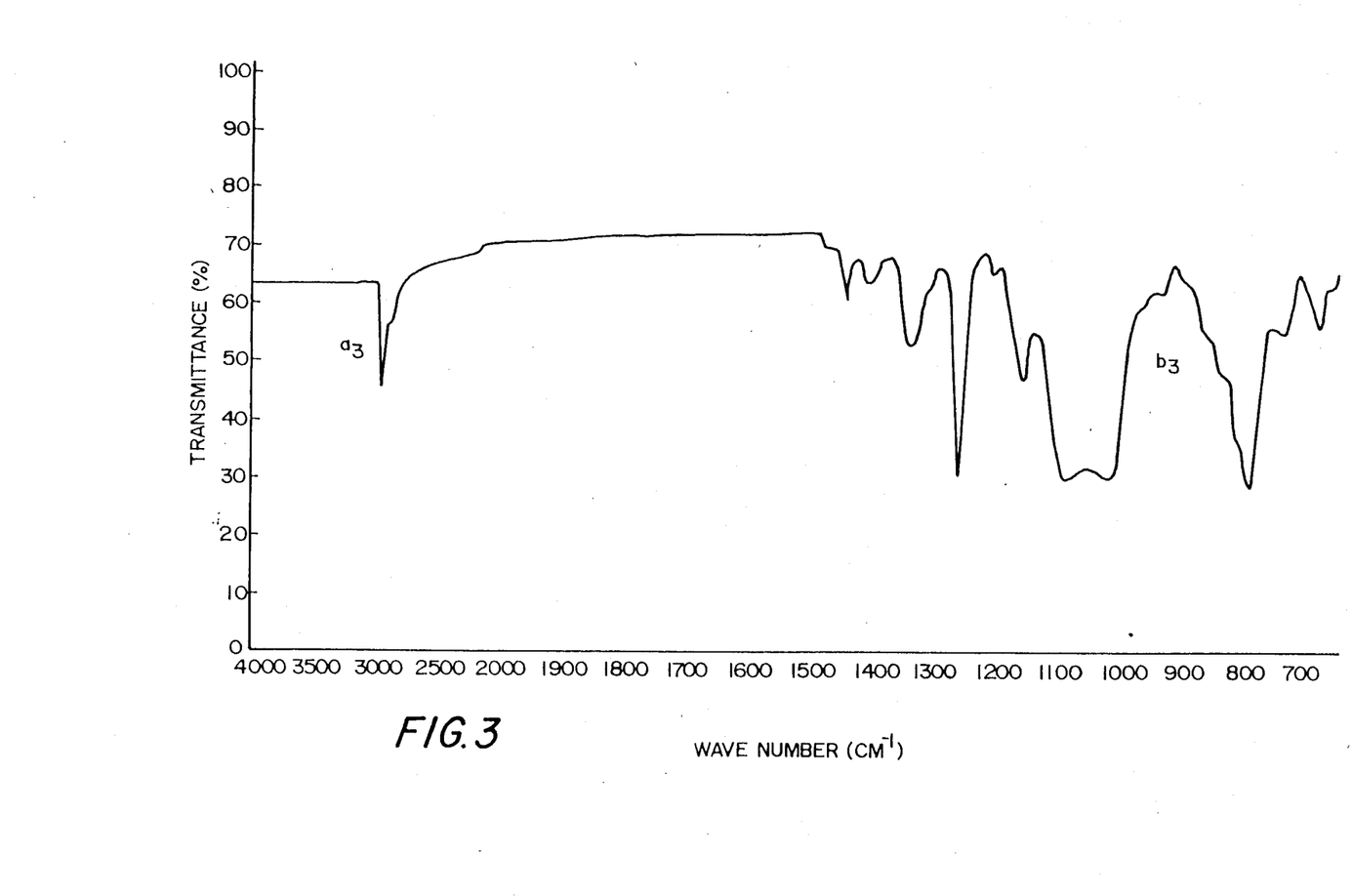
Figure 6:
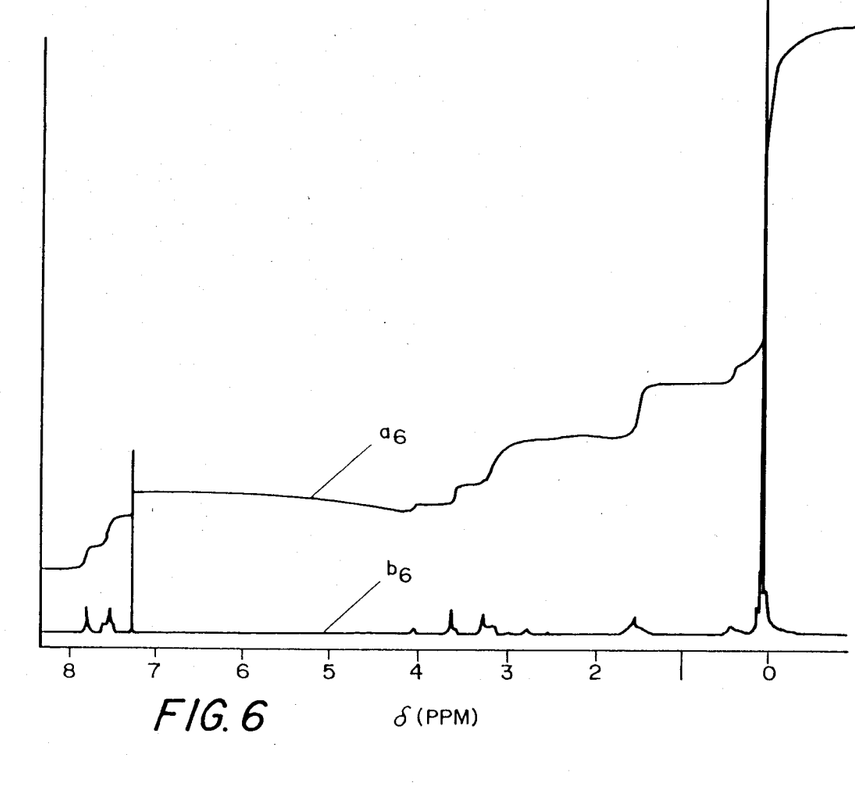

The identifying data of the obtained glycidyl sulfonamide compound (A-1) are shown in FIG. 3 and FIG. 6. FIG. 3 is a diagram showing the results of infrared absorption spectrum of the glycidyl sulfonamide compound (A-1) (measurement range: 650 to 4000 cm$^{-1}$, measured: neat). FIG. 6 is a diagram showing the results of proton nuclear magnetic resonance spectrum of the glycidyl sulfonamide compound (A-1) (NMR: 300 MHz, solvent: CDCl$_3$).

The peak $a_2$ at 3250 cm$^{-1}$:

in FIG. 2 disappears at $a_3$ in FIG. 3 and the peak $b_3$ at 930 cm$^{-1}$:

newly appeares in FIG. 3 in comparison with FIG. 2, which indicates that the proton of sulfonamide is substituted by a glycidyl group. In FIG. 6, the signal of 4.45 ppm: sulfonamide proton disappeares and the characteristic signals of 2.5 to 4.0 ppm newly appear, in comparison with FIG. 5. Near 2.5 to 4.0 ppm, besides the signals of 5 protons of glycidyl group, the signals of two protons of methylene group next to the nitrogen in formula (m) appear at the same place. The ratio of the integral intensity of the signals of 2.5 to 4.0 ppm to that of the protons of benzene ring is about 7:5, which indicates that the above identification of the glycidyl sulfonamide compound is valid ($a_6$ and $b_6$ indicate integral intensity and $\delta$, respectively).

(m)

With respect to the obtained glycidyl sulfonamide compound (A-1), the solubility in solvents at a room temperature and the compatibility with epoxy resins were investigated. The results are shown in Table

TABLE 1

| [Solubility of glycidyl sulfonamide compound (A-1)] | | | | |
|---|---|---|---|---|
| Solvent | Methanol | Chloroform | Ethyl acetate | |
| Solubility | ⊚ | ⊚ | | |
| Solvent | Toluene | Ethyl ether | | |
| Solubility | ⊚ | ⊚ | ⊚ | |
| Solvent | MIBK | n-Hexan | Water | EP828 (1) | TGDDM (2) |

TABLE 1-continued

[Solubility of glycidyl sulfonamide compound (A-1)]

| Solubility | ⊚ | X | X | X |
|---|---|---|---|---|

⊚: The compound is soluble in the solvent at suitable ratio.
X: The compound is not soluble in, or not compatible with the solvent.
(1) Available from Yuka Shell Epoxy Co., Ltd, under the trade name of "Epikote 828", epoxy equivalent weight: 189
(2) Tetraglycidyldiaminodiphenylmethane, epoxy equivalent weight: 120

EXAMPLE 2

[Preparation of glycidyl sulfonamide compound (A-2)]

The same procedure as in Preparation Example 1 was repeated except that 258.5 g of the sulfonamide compound (A-2) prepared in Preparation Example 2 was used instead of 63.15 g of the sulfonamide compound (A-1) to give 247.0 g of a glycidyl sulfonamide compound (hereinafter referred to as "glycidyl sulfonamide compound (A-2)"). The glycidyl sulfonamide compound (A-2) was also a liquid compound having a low viscosity at a room temperature and had an epoxy equivalent weight of 2978.

EXAMPLE 3

To 10.0 parts of the glycidyl sulfonamide compound (A-1) prepared in Example 1, was added 26.91 parts of 4,4'-diaminodiphenylmethane (hereinafter referred to as "DDM"), and the mixture was heated at 120° C. to melt and then was stirred for 10 minutes. Further, 100 parts of Epikote 828 (an epi-bis type epoxy resin having an epoxy equivalent weight of 189, available from Yuka Shell Epoxy Co., Ltd.) was added to the mixture. The mixture was mixed with heating to give a varnish, which was casted into a space between two glass plates set with inserting a spacer having a thickness of 3 mm. The thus molded varnish was cured with heating at 80° C. for 2 hours, at 120° C. for 2 hours, at 180° C. for 1 hour and then at 200° C. for 4 hours to give a cured bulky material.

The obtained cured bulky material was cut into test pieces having desired sizes by using a diamond cutter. The test pieces were subjected to measurements of heat distortion temperature (hereinafter referred to as "HDT"), bending test, izod impact test without notch, and pressure cooker test (hereinafter referred to as "PCT") at 120° C. and 2 atmospheres for 8 hours. The condition of pre-treatments of the test pieces and the method of measurements of properties of the material were carried out according to the method provided in JIS K 6911. With respect to the cured bulky material, the flexural strength and flexural elasticity were 9.2 kg/mm$^2$ and 287.4 kg/mm$^2$, respectively. The material having such properties as above can be sufficiently employed as a coating film.

COMPARATIVE EXAMPLE 1

A cured material was prepared in the same procedure as in Example 3 except that 100 parts of Epikote 828 and 26.23 parts of the DDM were mixed with heating to give a varnish. Then, the properties of the obtained cured material were measured.

COMPARATIVE EXAMPLE 2

A cured material was prepared in the same procedure as in Example 3 except that 100 parts of Epikote 828, 10 parts of a polypropylene glycoldiglycidylether (available from ASAHI DENKA KOGYO K.K. under the trade name of "ED 506", epoxy equivalent weight: 291) and 27.93 parts of DDM were mixed with heating to give a varnish. Then, the properties of the obtained cured material were measured in the same manner as in Example 3.

COMPARATIVE EXAMPLE 3

A cured material was prepared in the same procedure as in Example 3 except that 100 parts of the Epikote 828, 10 parts of a polyethyleneglycoldiglycidylether (available from Nippon Oil and Fats Co., Ltd. under the trade name of "E-100", epoxy equivalent weight; 142) and 29.72 parts of DDM were mixed with heating to give a varnish. Then, the properties of the obtained cured material were measured in the same manner as in Example 3.

COMPARATIVE EXAMPLE 4

A cured material was prepared in the same procedure as in Example 3 except that 100 parts of Epikote 828, 25.22 parts of DDM and 10 parts of the amine-modified silicone oligomer (available from CHISSO CORPORATION under the trade name of "SILAPLANE FM-3311", amine equivalent: 493 g/equivalent) were mixed with heating to give a varnish. Then, the properties of the obtained cured material were measured in the same manner as in Example 3.

With respect to the above-mentioned Example 3 and Comparative Examples 1 to 4, the amounts of constituents of the composition, the curing conditions and the results of measurements of the physical properties of the obtained cured materials are shown in Table 2.

TABLE 2

| | Composition (parts) | | | | | |
|---|---|---|---|---|---|---|
| | Epikote 828*[1] | DDM | Glycidyl sulfonamide compound (A-1) | ED-506*[2] | E-100*[3] | FM-3311*[4] |
| Ex. No. 3 | 100.0 | 26.91 | 10.0 | — | — | — |
| Comp. Ex. No. 1 | 100.0 | 26.23 | — | — | — | — |
| Comp. Ex. No. 2 | 100.0 | 27.93 | — | 10.0 | — | — |
| Comp. Ex. No. 3 | 100.0 | 29.72 | — | — | 10.0 | — |
| Comp. Ex. No. 4 | 100.0 | 25.22 | — | — | — | 10.0 |

| | Properties of cured bulky materials | | | | | |
|---|---|---|---|---|---|---|
| | | Bending test | | | Properties of cured bulky materials | |
| | HDT (°C., 18.5 kg/cm$^2$) | Flexural strength (kg/mm$^2$) | Modulus of flexural elasticity (kg/mm$^2$) | Elongation (%) | Izod impact test (kg · cm/cm) | Water absorption after PCT (%) |
| Ex. No. 3 | 158.4 | 9.2 | 287.4 | 5.1 | 35.9 | 1.76 |
| Comp. Ex. No. 1 | 168.3 | 10.4 | 351.2 | 4.8 | 20.2 | 1.66 |
| Comp. Ex. No. 2 | 138.7 | 11.3 | 335.9 | 5.1 | 24.9 | 1.97 |
| Comp. Ex. No. 3 | 145.2 | 11.8 | 364.9 | 4.9 | 21.1 | 1.95 |

TABLE 2-continued

| | | | | | | |
|---|---|---|---|---|---|---|
| Comp. Ex. No. 4 | 152.8 | 8.9 | 289.5 | 5.0 | 26.9 | 2.02 |

[Notes]
*[1] Epi-bis type epoxy resin, available from Yuka-Shell Epoxy Co., Ltd.
*[2] Polypropylene glycol diglycidyl ether, available from ASAHI DENKA KOGYO K.K.
*[3] Polyethylene glycol diglycidyl ether, available from Nippon Oil and Fats Co., Ltd.
*[4] Amine-modified silicone oligomer, available from CHISSO CORPORATION
*[5] Izot impact test without notch

EXAMPLE 4

The varnish prepared in Example 3 was applied onto a glass plate by using a bar coater to give a coating film having a thickness of 100 μm. The coating film was cured in the same conditions as in Example 3 and contact angle of the cured film to a waterdrop was measured. The results are shown in Table 3. The coefficient of dynamic friction between the obtained coating film and mirror polished SUS plate was measured according to the method provided in ASTM-D-1894-63. The results are shown in Table 3. The measurement was carried out by using a load cell at a pressure between the SUS plate and the cured film of 24 g/cm$^2$ and head speed of 50 mm/minute.

COMPARATIVE EXAMPLE 5

The same procedure as in Example 4 was repeated except that the varnish prepared in Comparative Example 1 was used to give a coating film. Then, the properties of the coating film were measured in the same manner as in Example 4. The results are shown in Table 3.

COMPARATIVE EXAMPLE 6

The same procedure as in Example 4 was repeated except that the varnish prepared in Comparative Example 2 was used to give a coating film. Then, the properties of the coating film were measured in the same manner as in Example 4. The results are shown in Table 3.

COMPARATIVE EXAMPLE 7

The same procedure as in Example 4 was repeated except that the varnish prepared in Comparative Example 3 was used to give a coating film. Then, the properties of the coating film were measured in the same manner as in Example 4. The results are shown in Table 3.

COMPARATIVE EXAMPLE 8

The same procedure as in Example 4 was repeated except that the varnish prepared in Comparative Example 4 was used to give a coating film. Then, the properties of the coating film were measured in the same manner as in Example 4. The results are shown in Table 3.

TABLE 3

| | Properties of coating films | |
|---|---|---|
| | Contact angle of coating film to a water drop $\theta$ (°) | Coeffecient of dynamic friction ($\mu$x) |
| Ex. No. 4 | 78.3 | 0.21 |
| Comp. Ex. No. 5 | 64.3 | 0.21 |
| Comp. Ex. No. 6 | 74.7 | 0.26 |
| Comp. Ex. No. 7 | 57.0 | 0.25 |
| Comp. Ex. No. 8 | 48.3 | 0.27 |

EXAMPLE 5

To 1.0 part of the glycidyl sulfonamide compound (A-1) was added 41.03 parts of DDM, and the mixture was heated at 120° C. to melt and then was stirred for 10 minutes. Further, 100 parts of tetraglycidyl diaminodiphenylmethane (epoxy equivalent weight: 121, hereinafter referred to as "TGDDM") was added to the mixture. The mixture was mixed with heating to give a varnish, which was casted into a space between two glass plates set with inserting a spacer having a thickness of 3 mm. The molded varnish was cured with heating at 80° C. for 2 hours, at 120° C. for 2 hours, at 180° C. for 1 hour and then at 200° C. for 4 hours to give a cured bulky material.

The obtained cured bulky material was cut into test pieces having desired sizes by using a diamond cutter. The test pieces were subjected to measurements of HDT, bending test, Izod impact test without notch. The results are shown in Table 4. The procedures of the pre-treatment of the test pieces and the measurement of properties of the cured material were carried out according to the method provided in JIS K 6911.

EXAMPLES 6 and 7

A cured material was prepared in the same procedure as in Example 5 except that 2.0 parts (Example 6) or 5.0 parts (Example 7) of the glycidyl sulfonamide compound (A-1) was added to 100 parts of TGDM, then a prescribed amount of DDM was added to each of the mixture to give each varnish. The properties of the each cured material were measured. The results are shown Table 4.

COMPARATIVE EXAMPLE 9

A cured material was prepared in the same procedure as in Example 5 except that 100 parts of TGDDM and 40.97 parts of DDM were mixed with heating to give a varnish. The properties of the obtained cured material matter were measured in the same manner as in Example 5. The results are shown in Table 4.

TABLE 4

| | Composition (parts) | | | |
|---|---|---|---|---|
| Ex. No. | TGDDM | Glycidyl sulfonamide compound (A-1) | DDM | Condition of curing |
| Comp. Ex. No. 9 | 100.0 | 0 | 40.97 | At 80° C. for 2 hours, at 120° C. for 2 hours, at 180° C. for 1 hour and then at 200° C. for 4 hours |
| 5 | 100.0 | 1.0 | 41.03 | At 80° C. for 2 hours, at 120° C. for 2 hours, |

TABLE 4-continued

| | | | | at 180° C. for 1 hour and then at 200° C. for 4 hours |
|---|---|---|---|---|
| 6 | 100.0 | 2.0 | 41.10 | At 80° C. for 2 hours, at 120° C. for 2 hours, at 180° C. for 1 hour and then at 200° C. for 4 hours |
| 7 | 100.0 | 5.0 | 41.30 | At 80° C. for 2 hours, at 120° C. for hours, at 180° C. for 1 hour and then at 200° C. for 4 hours |

| | Results of tests | | | | |
|---|---|---|---|---|---|
| Ex. No. | HDT (°C., 18.5 kg/cm$^2$) | Flexural strength (kg/mm$^2$) | Flexural elasticity (kg/mm$^2$) | Elongation (%) | Izod impact strength without notch (kg · cm/cm) |
| Comp. Ex. No. 9 | 238.8 | 11.1 | 401.6 | 3.3 | 10.5 |
| 5 | 238.8 | 13.3 | 429.5 | 4.7 | 22.5 |
| 6 | 238.0 | 13.4 | 411.3 | 4.8 | 14.7 |
| 7 | 236.5 | 12.7 | 406.5 | 3.5 | 12.7 |

EXAMPLE 8

A cured material was prepared in the same procedure as in Example 5 except that 2.0 parts of the glycidyl sulfonamide compound (A-1), 26.36 parts of DDM and 100 parts of Epikote 828 (an epi-bis type epoxy resin available from Yuka Shell Epoxy Co., Ltd., epoxy equivalent weight: 189) were mixed with heating to give a varnish. The properties of the cured material were measured in the same manner as in Example 5. The results are shown in Table 5.

COMPARATIVE EXAMPLE 10

A cured material was prepared in the same procedure as in Example 5 except that 100 parts of Epikote 828 and 26.23 parts of DDM were mixed with heating to give a varnish. The properties of the cured material were measured in the same manner as in Example 5. The results are shown in Table 5.

TABLE 5

| | Composition (parts) | | | |
|---|---|---|---|---|
| Ex. No. | Epikote 828 | Glycidyl sulfonamide compound (A-1) | DDM | Condition of curing |
| Comp. Ex. No. 10 | 100.0 | 0 | 26.23 | At 80° C. for 2 hours, at 120° C. for 2 hours, at 180° C. for 1 hour and then at 200° C. for 4 hours |
| 8 | 100.0 | 2.0 | 26.36 | At 80° C. for 2 hours, at 120° C. for 2 hours, at 180° C. for 1 hour and then at 200° C. for 4 hours |
| 9 | 100.0 | 5.0 | 26.57 | At 80° C. for 2 hours, at 120 C. for 2 hours, at 180° C. for 1 hour and then at 200° C. for 4 hours |
| 10 | 100.0 | 10.0 | 26.91 | At 80° C. for 2 hours, at 120° C. for 2 hours, at 180° C. for 1 hour and then at 200° C. for 4 hours |
| 11 | 100.0 | 20.0 | 27.59 | At 80° C. for 2 hours, at 120° C. for 2 hours, at 180° C. for 1 hour and then at 200° C. for 4 hours |

| | Results of tests | | | | |
|---|---|---|---|---|---|
| Ex. No. | HDT (°C., 18.5 kg/cm$^2$) | Flexural strength (kg/mm$^2$) | Flexural elasticity (kg/mm$^2$) | Elongation (%) | Izod impact strength without notch (kg · cm/cm) |
| Comp. Ex. No. 10 | 168.3 | 10.4 | 351.2 | 4.81 | 20.2 |
| 8 | 165.4 | 10.8 | 311 | 7.0 | 56.3 |
| 9 | 159.8 | 10.2 | 303 | 6.3 | 53.0 |
| 10 | 158.4 | 9.2 | 287.4 | 5.1 | 35.9 |
| 11 | 141.2 | 8.5 | 244 | 6.1 | 30.7 |

| | Results of tests | | | |
|---|---|---|---|---|
| Ex. No. | Initiation Temperature of thermal decomposition* (°C.) | Loss in weight at initiation temperature thermal decomposition* (%) | Temperature at Loss in weight of 10%* (°C.) | Loss in weight at 500° C.* (%) |
| Comp. Ex. No. 10 | 378 | 1.1 | 379 | 55.1 |
| 8 | 377 | 0 | 379 | 65.9 |
| 9 | 374 | 0.4 | 379 | 53.9 |
| 10 | 367 | 0.6 | 373 | 57.8 |
| 11 | 372 | 1.7 | 374 | 61.0 |

*Results of thermogravimetric analysis by means of a TGA apparatus of RTG-DTA type (II) made by RIGAKU DENKI Co., Ltd.
Rate of raising temperature: 10° C./minute, set temperature: room temperature to 500° C., under N$_2$ gas atmosphere The results are shown in Table 5.

EXAMPLES 9 to 11

A cured material was prepared in the same procedure as in Example 8 except that 5.0 parts (Example 9), 10.0 parts (Example 10) or 20.0 parts (Example 11) of the glycidyl sulfonamide compound (A-1) was added to 100 parts of Epikote 828, then a prescribed amount of DDM was added to each of the mixture to give each varnish. The properties of the each cured material were measured in the same manner as in Example 8. The results are shown in Table 5.

The glycidyl sulfonamide compound (A) of the present invention having a (poly)siloxane main chain in its molecule has much lower viscosity than that of usual epoxy resins and provides a flexible cured material having large elongation. The glycidyl sulfonamide compound (A) can be optionally mixed and co-cured with any other epoxy compound, and thereby, it becomes possible to impart flexibility and toughness to the cured material of the epoxy resin. When a glycidyl compound of (poly)oxyalkylene is used as a flexibilizer for epoxy resins, the properties of the cured material of the epoxy resins such as thermal resistance, chemical resistance and water absorption deteriorate. However, when the glycidyl sulfonamide compound (A) of the present invention is used, the impact strength of the cured material of the epoxy resin can be remarkably improved with controlling deterioration of the thermal resistance of the cured material to a minimum.

As mentioned above, since the glycidyl sulfonamide compound (A) of the present invention has excellent properties which cannot be found in usual epoxy resins or flexibilizers, the compound (A) is useful as, for instance, casting materials for electric or electronic apparatuses, paints, adhesive agents, matrix materials for laminated materials or FRP, and the like. Especially, since the glycidyl sulfonamide compound (A) brings both excellent thermal resistance and toughness to the conventional epoxy resins, and is effective in decreasing internal stress of the cured material, the compound (A) is expected to be used in the field of materials to which mechanical or thermal stresses should be repeatedly given.

With respect to the cured material of the epoxy resin composition of the present invention, the properties such as flexural strength, elongation and Izod strength can be remarkably improved since the epoxy resin composition contains the glycidyl sulfonamide compound (A). Deterioration of mechanical properties and thermal resistance of the cured material other than the above-mentioned properties is very small, therefore, there is not caused any problem in the practical uses thereof. The epoxy resin composition of the present invention can provide a cured material having both excellent toughness and thermal resistance, while conventional epoxy resins cannot provide a cured material having both toughness and thermal resistance at the same time.

Furthermore, because the resin composition for epoxy paint of the present invention contains the glycidyl sulfonamide compound (A) having a (poly)siloxane main chain of the molecule and the compound (A) contributes, as a rubber like component, to absorption of impact force, water repellency and lubrication on the surface of the cured material of the composition, the resin composition for an epoxy paint of the present invention has effects to provide an excellent coating film having higher mechanical strength, softness, water repellency and lubrication, and is more excellent in flexibility in comparison with conventional epoxy resin paints. Generally, when a glycidyl compound of (poly)oxyalkylene is used as a flexibilizer for paint, there occur deteriorations of properties such as increase of water absorption, increase of coefficient of friction and decrease of thermal resistance of the coating film. However, when the epoxy resin composition of the present invention is used for a paint, the deteriorations of the above-mentioned properties of the coating film can be controlled in such a low level that problems are hardly caused. Further, there is not caused bleed of the glycidyl sulfonamide compound (A).

The epoxy resin composition of the present invention is useful as paints, coating materials for electric or electronic apparatuses, or the like since the composition provides a coating film having excellent properties which cannot be found in conventional epoxy resin paints, as mentioned above.

What is claimed is:

1. An epoxy resin composition comprising:
   (A) the glycidyl sulfonamide compound represented by the formula $$\begin{array}{c} CH_2-CH-CH_2 \\ \diagdown \;\; / \\ O \end{array} \begin{array}{c} O \\ \diagdown \\ N-R^2-\underset{\underset{R^3}{|}}{\overset{\overset{R^3}{|}}{Si}}-O\!\!+\!\!\underset{\underset{R^3}{|}}{\overset{\overset{R^3}{|}}{Si}}-O\!\!\!+_{\!\!n}\!\!\underset{\underset{R^3}{|}}{\overset{\overset{R^3}{|}}{Si}}-R^2-N \\ / \\ R^1-S \\ \| \\ O \end{array} \begin{array}{c} X \\ \diagup \\ O \\ \diagdown \\ S-R^1 \\ \| \\ O \end{array} \quad (I)$$

wherein each $R^1$ is a monovalent hydrocarbon group having 1 to 20 carbon atoms, each $R^2$ is a bivalent hydrocarbon group having 1 to 6 carbon atoms, each $R^3$ is a monovalent hydrocarbon group having 1 to 6 carbon atoms, n is 0 or an integer of 1 to 70 and X is hydrogen atom or glycidyl group,
   (B) an epoxy resin and
   (C) a curing agent.

2. The epoxy resin composition of claim 1, wherein said composition is a resin composition for an epoxy paint.

3. The epoxy resin composition of claim 1, wherein the weight ratio of the glycidyl sulfonamide compound the (I) to the epoxy resin is from 0.01 : 99.99 to 50 : 50.

4. The epoxy resin composition of claim 1, wherein said epoxy resin is an epi-bis type epoxy resin.

5. The epoxy resin composition of claim 1, wherein said epoxy resin is an epoxy resin having at least one N,N-diglycidylamino group in its molecule.

6. The epoxy resin composition of claim 5, wherein said epoxy resin having at least one N,N-diglycidylamino group in its molecule is at least one member of tetraglycidylaminodiphenylmethane and a condensation product thereof.

7. The epoxy resin composition of claim 1, wherein said curing agent is an aromatic amine curing agent.

8. The epoxy resin composition of claim 1, wherein said curing agent is an aliphatic amine curing agent.

9. The epoxy resin composition of claim 1, wherein said curing agent is a polyamine having at least two primary amino groups in its molecule.

10. The epoxy resin composition of claim 9, wherein said polyamine is 4,4'- or 3,4'-diaminodiphenyl sulfone, or 4,4'- or 3,4'-diaminodiphenylmethane.

11. The epoxy resin composition of claim 1, wherein said curing agent is an acid anhydride curing agent.

12. A cured material prepared by curing the epoxy resin composition of claim 1.

13. The cured material of claim 12 in the form of a coating film.

* * * * *